(12) United States Patent
Castor et al.

(10) Patent No.: US 6,291,241 B1
(45) Date of Patent: Sep. 18, 2001

(54) **METHODS FOR MAKING *HYPERICUM* FRACTIONS AND ST. JOHN'S WORT PRODUCTS**

(76) Inventors: Trevor Percival Castor, 469 Mystic St., Arlington, MA (US) 02474; Theodore Abraham Tyler, 7 Circle Dr., Framingham, MA (US) 01702; Richard Joseph Student, 161 Old Westminster Rd., Hubbardston, MA (US) 01452

( * ) Notice: Subject to any disclaimer, the term of this patent is extended or adjusted under 35 U.S.C. 154(b) by 0 days.

(21) Appl. No.: 09/280,366

(22) Filed: Mar. 29, 1999

(51) Int. Cl.[7] .............. B01D 59/40; C02F 1/00; C12N 5/00; C12N 5/02
(52) U.S. Cl. .......... 435/410; 210/600; 210/767; 205/763
(58) Field of Search ............ 435/410; 210/600, 210/767; 60/647; 205/763

(56) References Cited

U.S. PATENT DOCUMENTS

| | | | |
|---|---|---|---|
| 5,164,308 | * 11/1992 | Kyle | 435/134 |
| 5,376,540 | * 12/1994 | Kyle | 435/134 |
| 5,440,055 | * 8/1995 | Castor | 549/510 |
| 5,466,434 | * 11/1995 | Kyle | 424/9 |
| 5,627,132 | * 5/1997 | LeBeau | 504/114 |
| 5,750,709 | * 5/1998 | Castor | 546/348 |
| 5,854,064 | * 12/1998 | Castor et al. | 435/308.1 |

OTHER PUBLICATIONS

Niesel et al., St. Johns Wort (*Hypercium perforatum L.*). Comparison of the Release of Hypericin and Pseudohypericin Accoridng to Different Extraction Conditions, Arch. Pharm., vol. 323, No. 9, 755see the abstract, 1990.*

* cited by examiner

*Primary Examiner*—Deborah K. Ware

(57) ABSTRACT

St. John's Wort products which have enhanced bioactivity in a serotonin re-uptake assay and enhanced stability are identified and manufactured from *Hypericum perforatum* biomass with supercritical and near critical fluids with and without polar cosolvents. These fluids are used to fractionate the biomass materials in several sequential steps. In each step, the biomass is subjected to a multiplicity of supercritical or near critical fluid extraction steps, with different solvation conditions used for each fraction. Thus, fractionation of the biomass is effected and the St. John's Wort products are manufactured. In addition to excellent overall yield, the bioactivity and stability of the St. John's Wort products manufactured from *Hypericum perforatum* biomass with supercritical and near critical fluids with and without polar cosolvents are significantly higher than that obtained by conventional organic phase extraction.

9 Claims, 3 Drawing Sheets

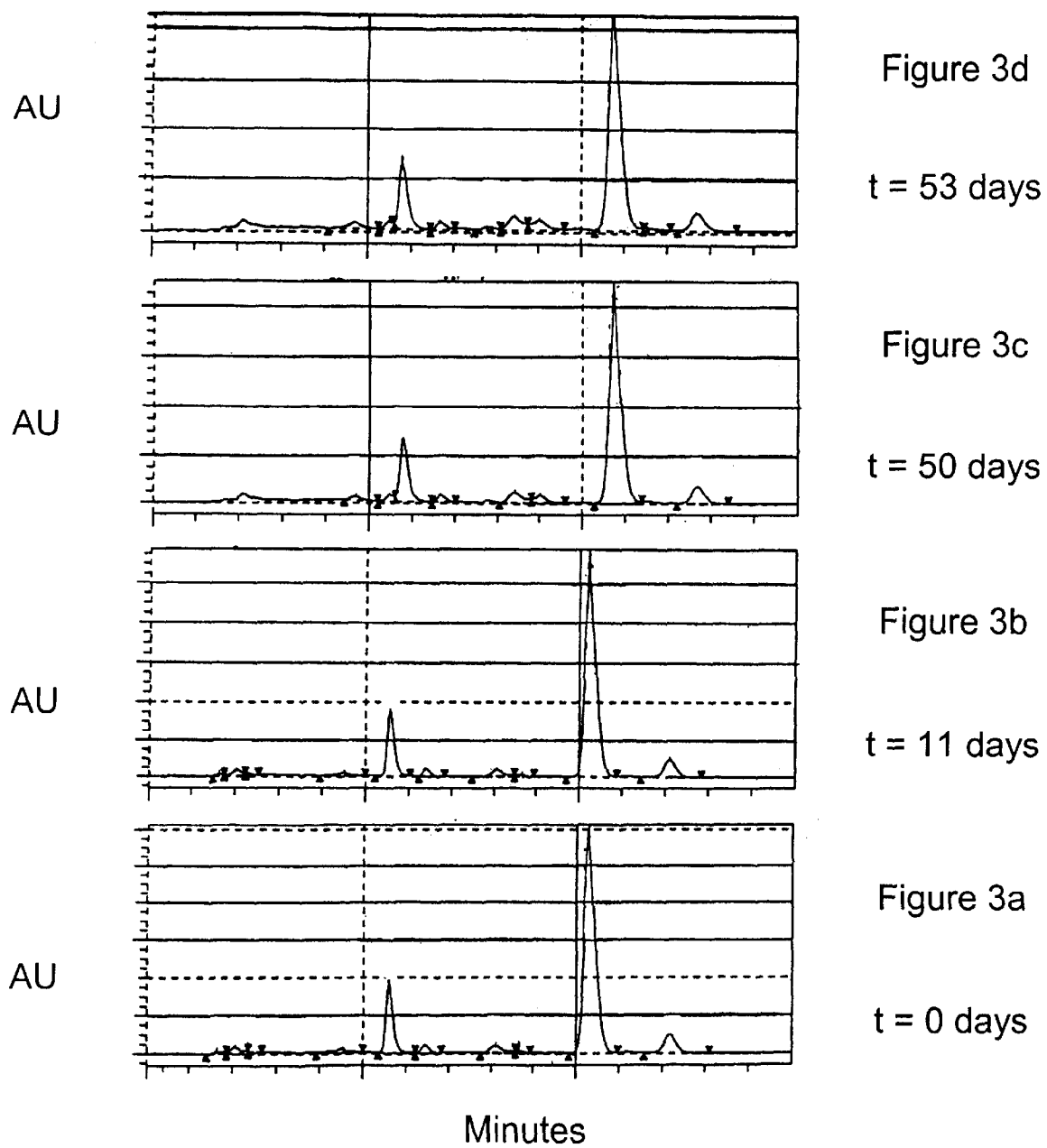

METHODS FOR MAKING *HYPERICUM* FRACTIONS AND ST. JOHN'S WORT PRODUCTS

FIELD OF THE INVENTION

This invention relates to methods for making Hypericum fractions and St. John's Wort products. The products contain one or more compounds which exhibit enhanced biological activities and enhanced product stabilities. The methods feature supercritical, critical and near critical fluids with and without polar cosolvents.

BACKGROUND OF THE INVENTION

St. John's Wort (*Hypericum perforatum* L.) is a bushy perennial with yellow flowers which blooms around St. John the Baptist's day in June. Commercial products are derived from the dried flowering tops or aerial parts of *Hypericum perforatum* L.; these parts are harvested shortly before or during the flowering period. Hypericum preparations include the dried herb (chopped or powdered), alcoholic extract, oil, and tincture.

Hypericum contains some very common plant constituents including flavonoid derivatives such as rutin, quercitrin and hypericin, biflavonoids such as amentoflavone, and essential oils. Active ingredients of Hypericum, which are specific to St. John's Wort, include the naphthodianthrones, such as cyclopseudohypericin, hypericin, hyperforin, isohypericin, photohypericin and psuedohypericin.

Hypericum extract has been used for the treatment of mild to moderate mental depression. All antidepressant medications made from St. John's Wort are based on methanol or ethanol extracts of the herb, with a solvent-to-herb ratio of 4:1 to 7:1. The highest yields of active antidepressant principles appear to be obtained by extracting the dried herb with aqueous methanol containing 20 to 40% water in darkness with temperatures raised only briefly to 60 to 80° C.

Hypericum oil is used in folk medicine as a traditional topical remedy for wounds and burns. Hypericum oil is typically made by macerating the ground fresh flowers in olive oil in a sealed vessel.

In folk medicine and traditional systems of medicine, various species of Hypericum have been used orally to treat anxiety, bedwetting, dyspepsia, excitability, exhaustion, fibrositis, gastritis, gout, hemorrhage, pulmonary complaints, rheumatism, sciatica, and swelling. It also has been used orally as anthelmintic, an antidiarrheal, and a diuretic. Various dosage forms of Hypericum have been used topically as an astringent and to treat injuries or conditions such as blisters, burns, cuts, hemorrhoids, inflammation, insect bites, itchiness, redness, sunburns, and wounds.

Hypericum with or without light therapy may be useful for the treatment of seasonal affective disorder but studies to date have used too few subjects to determine its efficacy. Light therapy combine with Hypericum may increase the risk of phototoxicity in light skinned patients. Hypericum is being combined with other products such as ma huang (ephedra) and promoted for weight loss as an alternative to prescription weight loss medications that have been taken off the market.

Some in vitro and in vivo studies have found that hypericum constituents may possess antiviral properties. In vitro studies suggest that hypericum constituents have antiviral activity against cytomegalovirus, herpes simplex, human immunodeficiency virus type 1, influenza virus A, Moloney murine leukemia virus, and sindbis virus. One in vivo study, in mice, found that low doses of hypericin and psuedohypericin prevented retroviral-induced diseases.

Of all the medical uses of St. John's Wort, the use of hypericum extracts for the treatment of mild to moderate depression is the most extensive. Standardized extracts of St. John's Wort are sold in pharmacies throughout Europe, and are in fact among the most popular OTC "phytomedicines" sold in EEC countries. Among the most widely prescribed antidepressants in the United States are Prozac® from Eli Lilly, Zoloft® from Pfizer and Praxil® from SmithKline Beecham. The worldwide sales of the top selling antidepressants are approximately $4.8 billion. As people experience adverse side-effects from prescription antidepressants, there has been a concomitant rise in the use of St. John's Wort and other herbs as natural antidepressants. Several herbal formulations, purporting to be natural substitutes for Prozac®, are already being marketed.

The alcohol extract of St. John's Wort enjoys a reputation as an effective antidepressant. The mechanisms of action by which the hypericum extract acts as an antidepressant are not fully understood. Some in vivo studies using, mouse or rat brain synatosomes have indicated that hypericum extract inhibits the synaptosomal uptake of serotonin, dopamine, and norepinephrine. Most in vivo studies have indicated that hypericum compounds competitively inhibit subtype A monoamine oxidase (MAO). Subtype A MAO inhibition, involving dopamine, norepinephrine, and serotonin, is thought to be effective in the treatment of depression. The National Institutes of Health has initiated a long term, multicenter, double-blinded clinical trial to study the effects of a hypericum extract (IL-160 manufactured by Kira), a placebo, and a selective serotonin re-uptake inhibitor (Zoloft which is manufactured by Pfizer) for the treatment of major depression.

IL-160, the most studied extract of Hypericum, is manufactured with 80% methanol in a solvent-to-herb ratio of 7–4:1 and standardized on 0.3 wt. percent content of hypericin. Recent findings indicate that *Hypericum perforatum* may have up to 10 active constituents with limited evidence that at least one of them, hyperforin, could be more active than hypericin. At least two manufacturers (of Perika and Movana tablets) are now standardizing their products against 3.0 wt. percent hyperforin. There are indications that hyperforin is very unstable and must be stabilized by the addition of excipients including antioxidants.

A method for producing fractions of Hypericum comprising different active ingredients or proportions of active ingredients is desired. Products incorporating such fractions could be marketed for different indications.

SUMMARY OF THE INVENTION

Embodiments of the present invention are directed to the methods of making fractions of Hypericum. The fractions can be used in the maimer of St. John's Wort products and Hypericum extracts.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero debyes. A supercritical fluid uniquely displays a wide spectrum of solvation power as its density is strongly dependent upon temperature and pressure. Temperature changes of tens of degrees or pressure changes by tens of atmospheres can change a compound's solubility in a supercritical fluid by an order of magnitude or more. This unique feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows a wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

While similar in many ways to conventional nonpolar solvents such as hexane, it is well-known that supercritical fluid solvents can extract a different spectrum of materials than conventional techniques. Product volatilization and oxidation as well as processing time and organic solvent usage can be significantly reduced with the use of supercritical fluid solvents.

A material at conditions that border its supercritical state will have properties that are similar to those of the substance in the supercritical state. These so-called "near critical" fluids are also useful for the practice of this invention. For the purposes of this invention, a near critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvins and psia. Table 1 shows how these requirements relate to some of the fluids relevant to this invention. To simplify the terminology, materials which are utilized under conditions which are supercritical, near critical, or exactly at their critical point will jointly be referred to as "SCCNC" fluids.

TABLE 1

Physical Properties of Critical Fluid Solvents

| Fluid | Formula | BP (° C.) | $P_{vap}$ (psia @ 25° C.) | $T_c$ (° C.) | $P_c$ (psia) | $0.75T_c$ (° C.) | $0.75P_c$ (psia) |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

Table 1 Notes:
BP = Normal boiling point; $P_{vap}$ = Vapor pressure

Embodiments of the present invention are directed to methods of making fractions of Hypericum. One method comprising the steps of contacting a Hypericum biomass with a first solvent comprising a critical, super critical or near critical fluid, to allow one or more first constituents of said Hypericum biomass to dissolve into the first solvent. The method further comprises the step of separating the first solvent from the Hypericum biomass to form a first fraction. The method further comprises the step of contacting the Hypericum biomass with at least one subsequent solvent comprising a critical, super critical or near critical fluid, to allow one or more additional constituents of the Hypericum biomass to dissolve into the subsequent solvent. The subsequent solvent is separated from said Hypericum biomass to form at least one subsequent fraction. The first solvent and at least one of the subsequent solvents have different salvation properties. The solvation properties are different due to at least one difference in one of the parameters of material of the first and subsequent critical, supercritical or near critical fluid, temperature, pressure, or concentration of entrainers and modifiers. Finally, the critical, supercritical and near critical fluid is removed from at least one of said first or subsequent fractions to form at least one concentrated fraction extract.

Preferably, each subsequent solvent is altered to change the solvation properties of the extracting fluid, so that each step can recover a different spectrum of compounds. The salvation properties of SCCNC fluids can be altered by changing the temperature or pressure of the fluid. By way of example, a preferred temperature and pressure for a SCCNC comprising carbon dioxide is a temperature in the range of 10 to 60° C. and a pressure in the range of 1,000 to 5,000 psig.

Preferred SCCNC fluids comprise carbon dioxide, nitrous oxide, ethylene, ethane, propane and fluoro-hydrocarbons. The fluid may also contain modifiers. Preferred modifiers are methanol, ethanol, propanol, butanol, methylene chloride, ethyl acetate and acetone.

A preferred modifier comprises methanol. In one preferred embodiment, each subsequent extraction employs a larger concentration of methanol. Thus, the plurality of solvents becomes increasingly more hydrophilic. The first extraction step tends to remove lipophilic compounds while the last extraction step tends to remove hydrophilic compounds. Removal of the lipophilic materials allows the next more hydrophilic critical fluid to have access to more hydrophilic compounds trapped in cellular structures. Preferred methanol concentration ranges, based on carbon dioxide at a pressure of 3000 psig and a temperature of 40° C., are 0–5 volume %. For the same temperature and pressure, 5–10 volume % methanol is preferred for a second extraction step; 10–20 volume % methanol is preferred for a third extraction step; 20–30 volume % methanol is preferred for a fourth extraction step; 30–50 volume % methanol is preferred for a fifth extraction step.

Surprisingly and unexpectedly, the sequential extraction with varying polarity solvents produces larger numbers of fractions exhibiting better biological activity and stability than corresponding fractions derived from conventional organic solvent extractions. The use of SCCNC fluids allows for easy removal of much of the solvent by mere depressurization. Use of a single apparatus to perform the sequential extraction or fractionation steps minimizes labor and increases efficiency. Indeed, the entire process can be readily automated. The use of SCCNC fluids allows the extraction conditions to be readily varied by temperature, pressure, or modifier solvents, minimizing equipment needs, processing time, potential for contamination, and loss of yield. These and other features and advantages will be readily apparent from the drawing and detailed discussion which follow.

BRIEF DESCRIPTION OF THE DRAWINGS

FIG. 3a shows of an HPLC chromatogram of the first SCCNC fluids St. John's Wort Fraction at time=0 days obtained through the practice of this invention.

FIG. 3b shows of an HPLC chromatogram of the first SCCNC fluids St. John's Wort Fraction at time=11 days obtained through the practice of this invention.

FIG. 3c shows of an HPLC chromatogram of the first SCCNC fluids St. John's Wort Fraction at time=50 days obtained through the practice of this invention.

FIG. 3d shows of an HPLC chromatogram of the first SCCNC fluids St. John's Wort Fraction at time=53 days obtained through the practice of this invention.

DETAILED DESCRIPTION OF PREFERRED EMBODIMENTS

Figure 1:
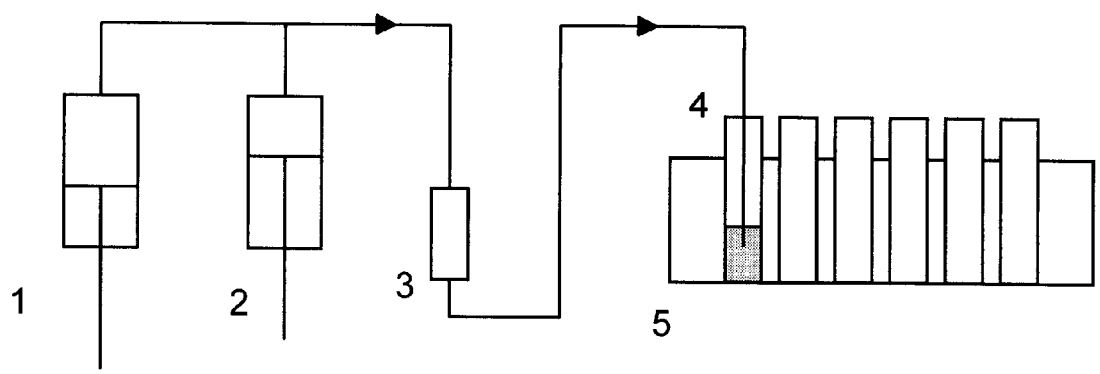
FIG. 1 shows a flow scheme for the SCCNC fractionation/extraction apparatus used in the examples of this specification.

SCCNC fluid fractionation can be carried out on an ISCO (Lincoln, Nebr.) SFX 3560 automated extractor or a manual version of the same. As shown in FIG. 1, this is a dual pump system, utilizing syringe pump 1 for neat critical fluid and syringe pump 2 for modifier. The pumps are independently controllable, allowing easy adjustment of the fluid composition. To prepare a sample, the Hypericum biomass was dried between 40 and 60° C. for 1 day, with or without vacuum and ground into a fine powder (around 100 mesh). The dried powder was transferred to a 10 ml ISCO extraction cartridge, numbered 3 in the figure, after which the cartridge was optionally filled with glass wool or cotton to reduce the dead volume. After loading a cartridge on the cartridge holder, the sequential extraction/fractionation procedure was commenced. The system was brought to 3,000 psig and 40° C. and extracted for 30 minutes with pure $CO_2$. This fraction was collected in methanol in a glass vial, numbered 4 in the figure. Next, the extraction parameters were set to: Supercritical $CO_2$ at 3000 psig and extraction temperature 40° C., step extractions with methanol as cosolvent at 5, 10, 20, and 40 vol %, each step being 10 min. Because some void volume remained, the composition of the extraction medium did not change sharply or immediately when modifier flowrate was adjusted to give a new fluid composition. Each sample thus yielded 5 fractions, which were collected in methanol in separate glass vials. The different collection vials are Mounted in a carousel, numbered 5 in the figure. The vials are automatically positioned by the SFX 3560 extractor apparatus. While the preceding steps were carried out in a continuous flow mode, cessation of flow to allow static contact time is also contemplated. This procedure may allow a reduction in the amount of extraction solvent required.

Several different experiments were conducted to evaluate the SCCNC fluids fractionation of Hypericum biomass and the resulting, St. John's Wort products.

EXAMPLES

Example 1

Fractionation of Hypericum Biomass with SCCNC Fluids

Dried Hypericum biomass (Lot# 335H699116), obtained from Wilcox Natural Products, Boone, N.C., was separated from twigs and branches. This material was ground to a fine powder. Three grams of dried and ground Hypericum biomass was fractionated with supercritical carbon dioxide and methanol at 3,000 psig and 40° C. The fractionation was carried out initially with neat carbon dioxide and then by incrementally adding methanol to increase the polarity of the working solvent. The extraction was carried out in an apparatus similar to that shown as FIG. 1. The fractions were dried under vacuum at approximately 40° C. for 18 hours. The results of the fractionation are shown in Table 2 below:

TABLE 2

Fractionation of Hypericum Biomass with SCCNC Fluids Carbon Dioxide/Methanol

| Fraction | Description | Amount Extracted (mg) | Percentage Extracted (%) |
|---|---|---|---|
| SJW-2A | Carbon Dioxide with 0% Methanol | 95.0 | 3.17 |
| SJW-2B | Carbon Dioxide with 5% Methanol | 16.6 | 0.55 |
| SJW-2C | Carbon Dioxide with 10% Methanol | 27.1 | 0.90 |
| SJW-2D | Carbon Dioxide with 20% Methanol | 90.8 | 3.01 |
| SJW-2E | Carbon Dioxide with 30% Methanol | 4.5 | 0.02 |
| SJW-2F | Carbon Dioxide with 40% Methanol | 6.0 | 0.02 |

Example 2

Biological Activity of SCCNC Fluids St. John's Wort Fractions

The first four fractions in Experiment SJW-2 in Example 1 above were dissolved in DMSO to 5 mg/ml; no insoluble matter was observed.

Rat brain synaptosomes were prepared from the cortex for $^3$H-5-HT uptake. Male Sprague-Dawley rats were decapitated and the brains were rapidly removed. Cortices were weighed and homogenized in 9 volumes of ice-cold 0.32M sucrose solution using a Potter-Elvejhem homogenizer. The homogenate was centrifuged at 1,000 g at 4° C. for 10 min. The supernatant was decanted and used for uptake experiments.

Fifty μl aliquots of the crude synaptosomal preparations were incubated in 1.2 ml of incubation medium at 37° C. of the following composition (mM concentrations): NaCl 109, KCl 3.55, $CaCl_2$ 2.4, $MgSO_4$ 0.61, $KH_2PO_4$ 1.1, $NaHCO_3$ 25, glucose 5.4, nialamide 0.025, pH 7.4 (this medium was gassed with 95% $O_2$-5% $CO_2$, 30 min prior to use) with $^3$H-5-HT. An incubation period of 5 min was employed. The uptake was stopped by dilution with 1.5 ml of ice-cold medium followed immediately by filtration under reduced vacuum through Whatman GF/B glass fiber filters. The filters were washed twice with 3 ml of ice-cold medium and dried. After addition of scintillant cocktail, $^3$H-radioactivity was counted. Stock solutions of test compounds prepared in DMSO, were centrifuged at 17,000×g for 10 min and the supernatants were used in the assays. Further dilutions were made in incubation medium.

Figure 2:
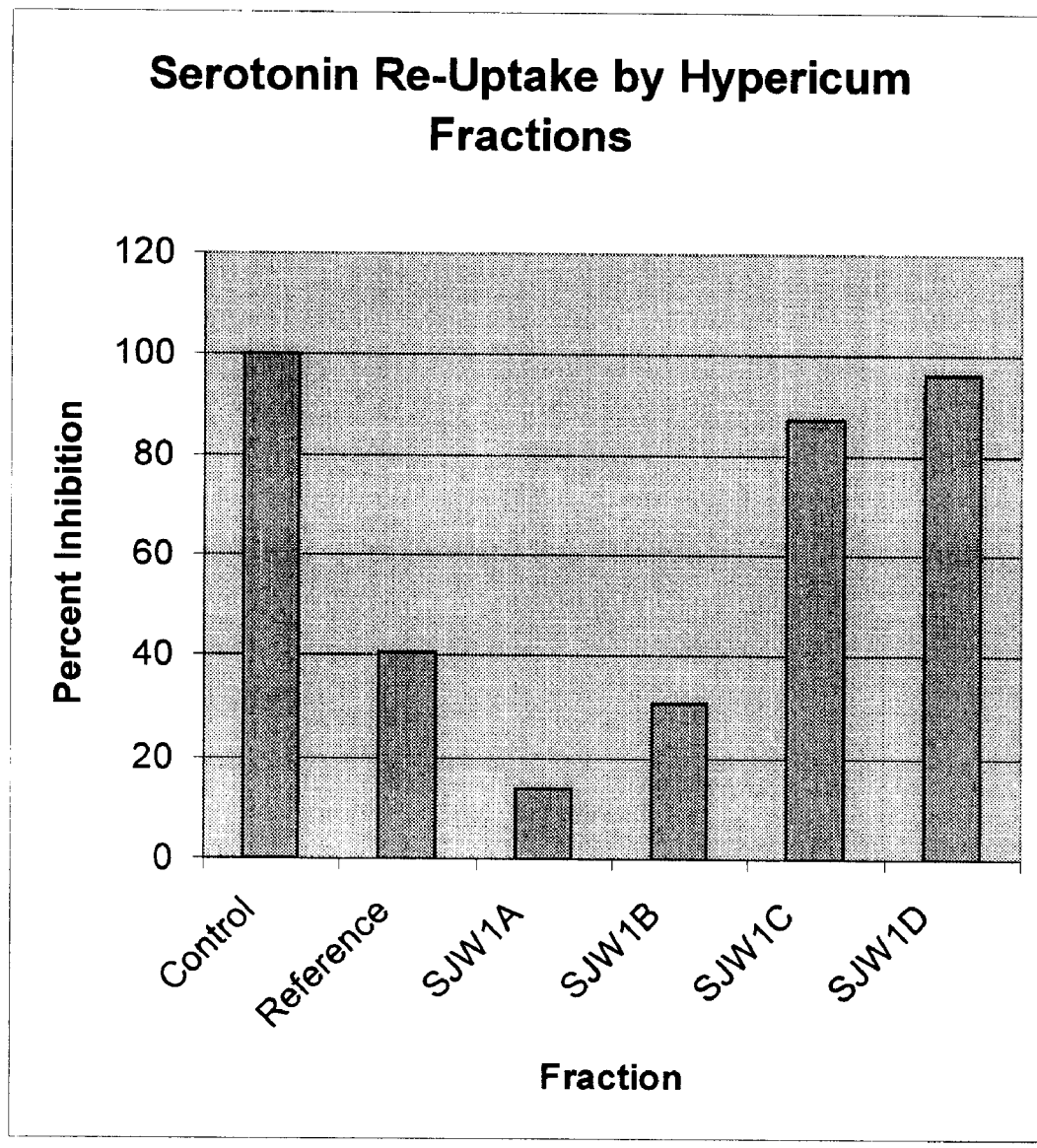
FIG. 2 shows the biological activities of SCCNC fractions obtained through the practice of this invention.

Samples were assayed in four replicates at a single dose of 16.7 μg/ml and compared to a reference extract (Perika tablets, Nature's Way St. John's Wort, Bar Code 33674-06560, Lot 710042, Expiration October 2000) at the same concentration in a serotonin specific re-uptake assay by Paracelsian, Ithaca, N.Y. This assay evaluates the re-uptake or the re-uptake inhibition (1—re-uptake) of radiolabeled serotonin taken up into a neural (syntaptosome) preparation in the presence of St. John's Wort fractions. The results are listed in Table 3 and shown in FIG. 2.

TABLE 3

Inhibition of Serotonin Re-Uptake by SCCNC Fluids St. John's Wort Fractions

| Fraction | Description | Mean Counts | Serotonin Re-Uptake (%) |
|---|---|---|---|
| Control | DMSO | 24,108 | 100.0 |
| Reference | Extract of Perika tablets | 9,792 | 40.6 |
| SJW-2A | Carbon Dioxide with 0% Methanol | 3,379 | 14.0 |
| SJW-2B | Carbon Dioxide with 5% Methanol | 7,381 | 30.6 |
| SJW-2C | Carbon Dioxide with 10% Methanol | 20,998 | 87.1 |
| SJW-2D | Carbon Dioxide with 20% Methanol | 23,140 | 96.0 |

SCCNC fluids fractions SJW-2A and SJW-2B are extremely potent compared to the reference Perika product. The first fraction SJW-2A is about three times more potent than the reference Perika tablets at the same concentrations.

Example 3

Chemistry of SCCNC Fluids St. John's Wort Fractions

HPLC assays were conducted on several SCCNC fluids St. John Wort's fractions, and a methanol extract of several Perika tablets. The assays were conducted with a MetaChem C18 column (25 cm×4.6 mm, 5 micron packing) and a 90% acetonitrile/$H_2O$ mobile phase with 500 microliters of a 5% (v/v) aqueous solution of 85% phosphoric acid per liter. The flowrate was 1.5 ml/min. Absorbance was monitored continuously from 200 nm to 395 nm using, a Waters Photo-Diode Array Detector in contour plot mode. Simultaneously, standard chromatographic scans were obtained using a wavelength of 265 nm.

The SCCNC fluids St. John Wort's fractions were prepared in the same manner as Examples 1 and 2, by fractionating 3 grams of St. John's Wort with supercritical carbon dioxide and methanol at 3,000 psig and 40° C. The fractionation was carried out initially with neat carbon dioxide and then by incrementally adding methanol to increase the polarity of the working solvent. Sample SJW-3A was extracted from Hypericum biomass with neat carbon dioxide at 3,000 psi and 40° C.; sample SJW-3B was extracted from the same biomass with 95:5::carbon dioxide:methanol at 3,000 psi and 40° C.; sample SJW-3B was extracted from the same biomass with 90:10::carbon dioxide:methanol at 3,000 psi and 40° C.; and sample SJW-3B was extracted from the same biomass with 80:20::carbon dioxide:methanol at 3,000 psi and 40° C.

A methanol extract of St. John's Wort was prepared by extracting 5 grams of St. John's Wort with 100 ml HPLC grade methanol at 50° C. The extraction was conducted with continuous stirring on a magnetic hot plate for more than 2 hours. The extractant was then filtered through a 0.45 micron Whatman filter to give a clear filtrate for analysis. The residue was re-extracted twice and analyzed. No actives were extracted in the subsequent extractions indicating that the first extraction was complete.

Ten Perika tablets (Nature's Way St. John's Wort, Bar Code 33674-06560, Lot 710042, Expiration October 2000) were weighed and ground into a fine powder. The ground tablets were extracted by stirring with 30 ml of 95% water/5% methanol mixture for 40 minutes. The extractant was then brought to 70 ml with a mixture of 92% methanol/8% water and mixed with a magnetic stir bar for 10 minutes. The extractant was filtered through a 0.45 micron Whatman filter and the filtrate transferred to a 100 ml volumetric flask. The solids were rinsed with a mixture of 92% water/8% methanol, and the rinse added to the 100 ml volumetric flask. The extracts were brought up to 100 ml and analyzed. The solids were re-extracted with an additional 12 ml of 92% methanol/8% water and filtered. The filtrate from the second extraction was analyzed but contained no actives. The solids from the second extraction were soaked in 2 ml of water, then mixed with 18 ml of 92% methanol/8% water and filtered. The filtrate from the third extraction was analyzed but contained no actives.

HPLC chromatograms of the first SCCNC fluids St. John Wort's fraction and the methanol extract of Perika tablets were compared. Hyperforin was readily identified from the UV spectrum in the paper by Hölzl and Ostrowski (1987) as eluting at 10.3 mins under the HPLC conditions used. The results of the fractionation of St. John's Wort with SCCNC carbon dioxide/methanol are listed in Table 4.

TABLE 4

Chemistry of SCCNC Fluids St. John's Wort Fractions

| Fraction | Amount Extracted (mg) | Percentage Extracted (%) | Hyperforin (mg) | Hyperforin Absolute Purity (%) | Hyperforin Chromat. Purity (%) |
|---|---|---|---|---|---|
| SJW-3A | 67.9 | 2.3 | 29.7 | 43.7 | 72.7 |
| SJW-3B | 70.9 | 2.4 | 23.1 | 32.6 | 72.8 |
| SJW-3C | 62.9 | 2.1 | 6.4 | 10.2 | 71.6 |
| SJW-3D | 75.6 | 2.5 | 2.6 | 3.4 | 71.0 |
| Total | 277.3 | 9.3 | 61.8 | ~20.6 | ~72.0 |

The chromatographic purities of hyperforin in the SCCNC St. John's Worth fractions A through D were between 71 and 73%, while the chromatographic purity of the Perika extract was about 7%.

Approximately 61.8 mg hyperforin was extracted from 3 grams of raw materials, giving a SCCNC fluids fractionation yield of approximately 20.6 mg/gm. A parallel warm methanol extraction of Hypericum biomass yielded approximately 21.0 mg/gram. The SCCNC fluids fractionation yielded about the same amount (approximately 100%) of hyperforin extracted from the same raw materials. However, the absolute (43.7%) and chromatographic purities (72.7%) of hyperforin in the SCCNC fluids St. John's Wort fraction A and the absolute (32.6%) and chromatographic (72.8%) purities of hyperforin in the SCCNC fluids St. John's Wort fraction B were much higher than the absolute (9.0%) and chromatographic (18.9%) purities of hyperforin in the methanolic Hypericum fractions.

Example 4

Chemical Solution Stability of SCCNC Fluids St. John's Wort Fractions

SCCNC fluids St. John Wort's Fraction A was analyzed by the assay described in Example 3. The HPLC chromatogram is shown as FIG. 3a. After analysis, the vial was re-capped and stored in its methanol solvent in a dark cabinet at room temperature. The sample was then re-analyzed after 11, 50 and 53 days utilizing an identical HPLC procedure. The chromatograms are shown as FIGS. 3b, 3c and 3d. As shown in FIG. 3 and listed in Table 5, the HPLC profiles and the quantity of the primary component, hyperforin, remain almost unchanged after 11 days in a methanol solution it room temperature. After 53 days, the hyperforin concentration had fallen to about 77% of its initial value without significant deterioration in quality.

TABLE 5

Chemical Solution Stability of SCCNC Fluids Carbon Dioxide/ Methanol St. John's Wort Fraction

| Time (days) | Hyperforin (ppm) | % Change in Hyperforin | Hyperforin Chromatographic Purity (%) | % Change in Hyperforin Chromatographic Purity (%) |
|---|---|---|---|---|
| 0 | 994 | 0.0 | 70.0 | 0.0 |
| 11 | 964 | −3.0 | 69.6 | −0.6 |
| 50 | 793 | −20.2 | 67.5 | −3.6 |
| 53 | 763 | −23.2 | 66.3 | −5.3 |

Example 5

Biological Stability of SCCNC Fluids St. John's Wort Fractions

Samples of SCCNC fluids St. John Wort's Fractions analyzed in Example 2 were subsequently re-analyzed for biological activities by a serotonin re-uptake assay identical to the assay described in Example 2 above. In the interval between analyses, the samples were stored at 4° C. except for two periods of overnight shipment on ice and several thaw cycles during chemical and biological analyses. The results of the analyses are listed in Table 6.

TABLE 6

Biological Stability of Serotonin Re-Uptake Inhibition by SCCNC Fluids St. John's Wort Fractions

| Fraction | Description | Serotonin Re-Uptake (%) time = 6 days | Serotonin Re-Uptake (%) time = 71 days |
|---|---|---|---|
| Control | DMSO | 100.0 | 100.0 |
| SJW-2A | Carbon Dioxide with 0% Methanol | 14.0 | 13.5 |
| SJW-2B | Carbon Dioxide with 5% Methanol | 30.6 | 47.6 |
| SJW-2C | Carbon Dioxide with 10% Methanol | 87.1 | 72.8 |
| SJW-2D | Carbon Dioxide with 20% Methanol | 96.0 | 96.4 |

It is intended that the matter contained in the preceding description be interpreted in an illustrative rather than a limiting sense.

What is claimed is:

1. A method of making fractions of Hypericum, which fractions comprise hyperforin, comprising the steps of:

a.) contacting a Hypericum biomass with a first solvent comprising a critical, supercritical or near-critical fluid, to allow hyperforin to dissolve into the solvent;

b.) separating said first solvent from said Hypericum biomass to form a first fraction;

c.) contacting said Hypericum biomass with at least one subsequent solvent comprising a critical, supercritical or near-critical fluid, to allow hyperforin to dissolve into said at least one subsequent solvent;

d.) separating said subsequent solvent from said Hypericum biomass to form at least one subsequent fraction, wherein said first solvent and said at least one subsequent solvent have different solvation properties, wherein said solvation properties are different due to at least one difference in one of the parameters of material of the first and subsequent critical, supercritical or near-critical fluids, temperature, pressure, or concentration of entrainers and modifiers; and, e.) removing said critical, supercritical and near critical fluid from at least one of said first or subsequent fractions to form at least one concentrated fraction extract containing hyperforin.

2. The method of claim 1 wherein said critical, super critical or near critical fluid is formed with one or more of the group of materials consisting of carbon dioxide, nitrous oxide, ethylene, ethane, propane and fluoro-hydrocarbons.

3. The method of claim 1 wherein said entrainers and modifiers are selected from the group consisting of methanol, ethanol, propanol, butanol, methylene chloride ethyl acetate and acetone.

4. The method of claim 1 wherein said first solvent has a concentration of an entrainer up to and including 5% volume, and at least one of said subsequent solvent has a concentration of an entrainer and modifier from 5% to and including 10% volume.

5. The method of claim 4 wherein said entrainer and modifier is methanol.

6. The method of claim 1 wherein said critical, super critical or near critical fluid is carbon dioxide at 10 to 60 degrees centigrade at 1,000 to 5,000 psig.

7. A concentrated fraction extract containing hyperforin made by the process of claim 1.

8. The method of claim 1 wherein the step of contacting said Hypericum biomass with at least one subsequent solvent comprising a critical, supercritical or near-critical fluid to allow hyperforin to dissolve into said at least one subsequent solvent, comprises more than one subsequent solvent in which each of the subsequent solvent has a concentration of entrainers and modifiers from 5% to 50% by volume, said concentrations increasing with each subsequent solvent by 5 to 20% by volume.

9. A method of making a fraction of Hypericum, wherein said fraction comprises hyperforin, comprising the steps of:

a.) contacting a Hypericum biomass with a first solvent comprising a critical, supercritical or near-critical fluid, to allow hyperforin to dissolve into the solvent;

b.) separating said first solvent from said Hypericum biomass to form a first fraction; and, c.) removing said critical, supercritical or near critical fluid from said first fraction to form a fraction extract containing hyperforin.

* * * * *